United States Patent [19]
Henderson

[11] Patent Number: 5,296,476
[45] Date of Patent: Mar. 22, 1994

[54] SKIN CARE COMPOSITIONS

[76] Inventor: Esther G. Henderson, 11641 Harrells Ferry Rd., Apt. D, Baton Rouge, La. 70816

[21] Appl. No.: 693,037

[22] Filed: Apr. 30, 1991

Related U.S. Application Data

[63] Continuation-in-part of Ser. No. 404,660, Sep. 8, 1989, abandoned.

[51] Int. Cl.$^5$ .................. A61K 31/60; A61K 31/61
[52] U.S. Cl. .................... 514/163; 514/159; 514/574
[58] Field of Search .............. 514/159, 163, 574; 424/547

[56] References Cited

U.S. PATENT DOCUMENTS 4,393,045  7/1983  Henderson et al. .............. 424/95
4,608,370  8/1986  Aronshon ...................... 514/159

OTHER PUBLICATIONS

Chemical Abstracts 101:78673v & 78674w (1986).
The Handbook of Non Prescription Drugs, 5th ed 1977, pp. 361–364 & 378–379.

Primary Examiner—Leonard Schenkman

[57] ABSTRACT

The present invention relates to a topical skin care formulation comprised of micronized calcium citrate and salicylic acid. This composition provides a method for treating acne as well as providing for a variety of skin beautification products which are especially applicable to sensitive skin.

5 Claims, No Drawings

SKIN CARE COMPOSITIONS

This application is a continuation-in-part, of U.S. patent application Ser. No. 07/404,660 filed Sep. 8, 1989.

FIELD OF THE INVENTION

The present invention relates to a topical skin care formulation comprised of micronized calcium citrate and salicylic acid. This composition provides a method for treating acne as well as providing for a variety of skin beautification products which are especially applicable to sensitive skin.

BACKGROUND OF THE INVENTION

Skin care formulations have been previously formulated utilizing a great variety of components including salicylic acid. For example, U.S. Pat. Nos. 3,265,571, 4,318,907, 2,942,008 and 3,236,730 all disclose formulations which incorporate salicylic acid in their acne treating compositions calcium citrate is also found in a variety of products and is included in the "Generally Regarded as Safe" (GRAS) classification by U.S. Food and Drug Administration. It has been utilized as a source of calcium for humans rather than as an active ingredient in medications. An exception to its use as a medicament is U.S. Pat. No. 2,719,811 which discloses the use of a variety of water soluble metal complexes including calcium citrate which is used as a stimulating agent for cellular respiration.

The applicant of the instant formulation holds U.S. Pat. No. 4,393,045, which is a process in which the lining of mollusk shells were admixed with the extrudate of citric acid and was found to be effective in the treatment of skin care symptoms such as acne. After the issuance of the above patent, applicant found that it would be advantageous to include a keratolytic agent such as salicylic acid in the composition. The inventor found that by combining the calcium citrate with salicylic acid in the manner shown herein, that the results effected by each ingredient alone, were enhanced, not only as to effectiveness but also as the variety of application for skin care and topical analgesic products.

No patents to the knowledge of applicant have recognized the synergistic combination of calcium citrate and salicylic acid in the formulation of skin care and beautification products especially in regard to their utility in the cosmetic, detergent and topical remedy treatment of sensitive skin.

DETAILED DESCRIPTION OF THE INVENTION

The skin care composition of the present invention are characterized by the active ingredients calcium citrate and salicylic acid. This composition can be applied topically in the form of creams, masques, ointments, emulsions, lotions, gels, soaps, soap-free medication cleansing bars and the like.

The calcium citrate component of the instant formulation is effective only when utilized in the form of a micronized powder. The use of the calcium citrate alone, in such micronized state was found to be an effective treatment of skin care disorders such as acne. Applicant discovered that by blending of calcium citrate and salicylic acid, in the percentages shown in the examples, it produced results more effective as to each ingredient utilized alone. The characteristics of the preferred micronized powder are displayed in Table 1 for a tricalcium citrate powder which is commercially available form numerous sources.

TABLE 1

| Tricalcium Citrate USPXX Powder | |
|---|---|
| Molecular Formula: | $Ca_3(C_6H_5O_7)_2 \cdot 4H_2O$ |
| Molecular Weight: | 570.50 |
| Appearance: | White Powder |
| Identity: | Shows characteristic reactions of Calcium and Citrates |
| Solubility: | Very poorly soluble in water; soluble in diluted hydrochloric acid and nitric acid |
| Insoluble Parts of Hydrochloric Acid: | Max. 0.05% |
| Calcium Oxide ($CaCO_3$): | Trace |
| Heavy Metals (as Pb): | Max. 0.002% |
| Loss on Drying: | Max. 0.0006% |
| Assay: | 97.5-101.0% $Ca_3(C_6H_5O_7)_2$ calculated on the dry matter |
| Mesh Size Specification: | 94% through a #100 to #200 sieve |

As shown above it was determined to be advantageous to include keratolytic agent in the composition of the present invention. The preferred keratolytic agent for use in the instant invention is salicylic acid. The amount of salicylic acid employed in the skin care formulations of the instant invention can vary according to the specific desired skin care treatment.

Topical acne medication and skin beautification formulations for use in the present invention can be applied through the use of any suitable conventional vehicle or carrier. Convenient liquid vehicles which are useful in the application of the instant skin care formulations include water, alcohols, such as methanol, ethanol, propanol and isopropanol, water-alcohol solutions or water-alcohol-polyalkyleneglycol solutions. A convenient vehicle for the administration of the subject skin-treatment formulations of the instant invention is a water-ethanol-ethylene glycol solution having a weight composition of 50% water, 30% ethanol and 20% propyleneglycol.

The combination of calcium citrate and salicylic acid provides for a wide variety of skin beautification products. The foremost application of these ingredients is for the preparation of an acne medication. The present invention has additional cosmetic and skin beautification applications as an ingredient in skin moisturizers, sun-screens, pre-shave lotions, after-shave lotions, colognes, soap-free medicated cleansing bars, soaps, deodorants, athlete's foot and jock itch medications and wart and hard and soft corn removers. The utilization of the skin care formulation ingredients of the present invention in any of these applications is considered within the scope of the instant invention.

The compositions that are found to be the most therapeutically effective in the treatment of inflammation of the skin, including acne, is: micronized calcium citrate in an amount ranging from approximately 2 to 50 percent by weight and salicylic acid in an amount ranging from 0.05 to 2 percent by weight of the total composition which includes suitable carriers and the like.

Various different cosmetic and therapeutic applications require varying amounts of calcium citrate and salicylic acid according to the desired end product. The typical acne medicaments of the instant invention utilize 2.5% to 50%, preferably 5 to 40% by weight of calcium citrate and 0.05% to 2.0%, preferably 0.5 to 2.0% by weight salicylic acid as active ingredients.

Fast acting external analgesics can be formulated utilizing from 2.5% to 97% by weight of calcium citrate and about 0.2 to 2% by weight of salicylic acid. Corn removing agents can be formulated utilizing by weight of 2.5% to 97% calcium citrate and about 1% to 20% by weight of salicylic acid. Each formulation can be admixed with a suitable pharmaceutical carrier as are known in the art.

Topical skin treating compositions including sunscreens and non-oily moisturizers advantageously contain 3 to 20% by weight of micronized calcium citrate. These compositions may optionally contain 0.05 to 2% by weight of salicylic acid.

The instant delivery system may also include additional fragrance oils, moisturizers, humectants, emollients and other skin care and cosmetic ingredients, such as excipients, colorants, preservatives, diluents and the like.

It has been determined that the above components when combined in the ranges of proportions in the following examples synergistically provide skin treating compositions which result in skin beautification. In the examples displaying two part compositions A and B, both parts are suitably blended to produce a final applicable product. All percentages are percents by weight unless otherwise indicated.

| Example 1 | % by Weight | Preferred % |
|---|---|---|
| ACNE MEDICATION - LIQUID | | |
| Micronized Calcium Citrate from Table 1 | 5 to 20 | 10 |
| Salicylic Acid | .05 to 2 | .05 |
| Water (deionized) | 50 to 80 | 70 |
| Ethylalcohol | 5 to 20 | 10 |
| ACNE MEDICATION - GEL | | |
| Micronized Calcium Citrate | 20 to 35 | |
| Salicylic Acid | .05 to 2 | |
| Ethanol | 5 to 20 | |
| Bentonite | Up to 10% | |
| Silicone Fluid (e.g., Dow 556) | Up to 10% | |
| Hydroxyethyl Cellulose | Up to 5% | |
| Water | Remainder | |
| ACNE MEDICATION - CREAM | | |
| Micronized Calcium Citrate | 5 to 40 | |
| Salicylic Acid | .05 to 2 | |
| Bentonite | Up to 10% | |
| Oleth 3-Phosphate | Up to 5% | |
| Petrolatum | Up to 15% | |
| Carboner 934 | Up to 3% | |
| Benzyl Alcohol | Up to 3% | |
| Water | Remainder | |
| ACNE MEDICATION - OINTMENT | | |
| Micronized Calcium Citrate | 5 to 35% | |
| Salicylic Acid | .05 to 2% | |
| Polyethylene Glycol 4000 | 15 to 25% | |
| Cetyl Stearyl Glycol | Up to 5% | |
| Isopropyl Myristate | 25 to 35% | |
| Benzyl Alcohol | 1 to 3% | |
| Isopropyl or Ethylalcohol | 10 to 25% | |
| PRE-SHAVE LOTION | | |
| Micronized Calcium Citrate | 3 to 20% | |
| Salicylic Acid | .05 to 2% | |
| Ethyl Alcohol | 10 to 30% | |
| Water | Remainder | |
| AFTER-SHAVE LOTION | | |
| Micronized Calcium Citrate | 3 to 20% | |
| Salicylic Acid | .05 to 2% | |
| Fragrance | 10% | |
| Ethyl Alcohol | 20% | |
| Water | Remainder | |
| SKIN MOISTURIZER | | |

| Example 1 | % by Weight | Preferred % |
|---|---|---|
| Micronized Calcium Citrate | 5 to 20% | |
| Salicylic Acid | .05 to 2% | |
| Ethyl Alcohol | 20% | |
| Glycerine | 10% | |
| Water | Remainder | |
| SUNSCREEN | | |
| Micronized Calcium Citrate | 5 to 20% | |
| Salicylic Acid | .05 to 2% | |
| Oetyldimethylp-aminobenzoic-acid (sunscreen) | 15% | |
| Ethyl Alcohol | 20% | |
| Water | Remainder | |
| SOFT CORN REMOVER | | |
| Micronized Calcium Citrate | 10% to 40% | |
| Bentonite | 5% | |
| Salicylic Acid | 2 to 10% | |
| Ethyl Alcohol | 30% | |
| Propylene Glycol | 1 to 5% | |
| Water | Remainder | |
| HARD CORN REMOVER | | |
| Micronized Calcium Citrate | 10% to 40% | |
| Salicylic Acid | 10 to 20% | |
| Ethyl Alcohol | 30% | |
| Bentonite | 5% | |
| Water | Remainder | |
| SOAP | | |
| Micronized Calcium Citrate | 2 TO 10% | |
| Salicylic Acid | .05 to 2% | |
| Soap Stock | 30% | |
| Water | Remainder | |
| COLD CREAM | | |
| Micronized Calcium Citrate | 3% to 20% | |
| Salicylic Acid | .05 to 2% | |
| Liquid Paraffin | 5% | |
| Beeswax | 5% | |
| Water | Remainder | |

The following specific examples display preferred product produced in accordance with the instant invention.

| | Parts By Weight | % |
|---|---|---|
| EXAMPLE 2 | | |
| Pre-Shave Condition for Topical Analgesic | | |
| Component A | | |
| Calcium Citrate | 600 | 20.0 |
| Rhodigel 23 | 24 | .8 |
| Collagen | 30 | 1.0 |
| Germaben II | 30 | 1.0 |
| Deionized Water | 1573.2 | 52.4 |
| Component B | | |
| Ethanol SD 408 | 600 | 20.0 |
| Stearic Acid | 22.8 | .8 |
| Cetyl Alcohol | 12 | .4 |
| Isopropyl Myristate | 30 | 1.0 |
| Solulan 98 | 30 | 1.0 |
| Salicylic Acid | 45 | 1.5 |
| TOTAL A & B | 3000 | 100% |
| EXAMPLE 3 | | |
| UNIVERSAL ACNE MASQUE | | |
| Component A | | |
| Calcium Citrate | 2240.0 | 28.0 |
| Bentonite | 800.0 | 10.0 |
| Lo-Micron Pink | 3.2 | .0 |
| Component B | | |
| Citric Acid | 160.0 | 2.0 |
| Salicylic Acid | 80.0 | 1.0 |
| Potassium Sorbate | 6.4 | .0 |
| Deionized Water | 4310.4 | 54.0 |
| Component C | | |
| SD Alcohol 40 | 400.0 | 5.0% |
| TOTAL A,B & C | 8000.0 | 100% |
| EXAMPLE 4 | | |

-continued

| | Parts By Weight | % |
|---|---|---|
| Acne Medication | | |
| Component A | | |
| Calcium Citrate | 400.0 | 10.0% |
| Talc | 60.0 | 1.5 |
| Kaolin | 36.0 | .9 |
| Titanium Dioxide | 24.0 | .6 |
| Methocel E-4M | 4.8 | .2 |
| Clark Pigments | | |
| 7076 | 5.6 | .4 |
| 7055 | 4.0 | .1 |
| 7133 | 2.4 | .06 |
| Component B | | |
| Propylene Glycol | 120.0 | 3.0% |
| Salicylic Acid | 19.2 | .5 |
| SD Alcohol 40 | 400.0 | 10.0 |
| Citric Acid | 64.0 | 1.6 |
| Potassium Sorbate | 3.2 | .08 |
| Deionized Water | 2856.8 | 71.4 |
| TOTAL COMPOSITION A & B | 4000.0 | 100.0% |

EXAMPLE 5
ACNE MEDICATION

| | Parts By Weight | % |
|---|---|---|
| Component A | | |
| Calcium Citrate | 2800.0 | 35.0 |
| Bentonite | 400.0 | 5.0 |
| Lo-Micron Pink | 3.2 | .04 |
| Component B | | |
| Citric Acid | 192.0 | 2.4 |
| Salicylic Acid | 120.0 | 1.5 |
| Potassium Sorbate | 6.4 | .08 |
| Propylene Glycol | 160.0 | 20.0 |
| Deionized Water | 3518.4 | 44.0 |
| Component C | | |
| SD Alcohol 40 | 800.0 | 10.0 |
| TOTAL A, B & C | 8000.0 | 100.0% |

EXAMPLE 6
SUNSCREEN

| | Parts By Weight | % |
|---|---|---|
| Component A | | |
| Micronized Calcium Citrate | 12.5 | |
| Rodigel 23 (Xanthan Gum Thick) | 2.0 | |
| Aloe Gel | 25.0 | |
| Potassium Sorbate | 0.5 | |
| Tetraethylamine (TEA) | 1.25 | |
| Water | 176.25 | |
| Component B | | |
| Ethanol | 25.0 | |
| Stearic Acid | 5.0 | |
| Catyl Alcohol | 2.5 | |
| Escalol 507 (2-ethylhexyl salicylate) | 12.5 | |
| Total A & B | 262.50 | |

EXAMPLE 7
NON-OILY MOISTURIZER

| | Parts By Weight | % |
|---|---|---|
| Component A: | | |
| Micronizd Calcium Citrate | 12.5 | |
| Rhodigel 23 | 2.0 | |
| Aloe Gel | 50.0 | |
| Tea | 0.25 | |
| Collagen | 5.0 | |
| Potassium Sorbate | 0.5 | |
| Deionized Water | 134.5 | |
| Component B | | |
| Ethanol | 37.5 | |
| Stearic Acid | 2.0 | |
| Cetyl Alcohol | 1.0 | |
| Dow 225 | 2.5 | |
| Isopropyl Myristate | 2.5 | |
| Vitamin E | 0.2 | |
| Total A & B | 250.45 | |

I claim:

1. A method for removing soft corns in a human having a skin affected thereby comprising administering topically to the affected skin a therapeutically effective amount of micronized calcium citrate and salicylic acid.

2. The method of claim 1 wherein the therapeutically effective amount comprises 10 to 40% by weight of micronized calcium citrate and 2.0 to 10% by weight of salicylic acid.

3. A method for removing corns in a human having a skin affected thereby comprising administering a therapeutically effective amount of micronized calcium citrate and a keratolytic agent in a suitable carrier.

4. The method of claim 3 wherein the keratolytic agent is salicylic acid.

5. The method of claim 3 wherein the therapeutically effective amount comprises 2.5 to 97% by weight of micronized calcium citrate and 1 to 20% by weight of the salicylic acid.

* * * * *